(12) United States Patent
Maracas et al.

(10) Patent No.: US 7,613,488 B1
(45) Date of Patent: Nov. 3, 2009

(54) APPARATUS AND METHODS FOR COMPENSATION OF BLOOD VOLUME EFFECTS ON NIR SPECTROSCOPIC MEASUREMENTS OF BLOOD ANALYTES

(75) Inventors: George N. Maracas, Phoenix, AZ (US); Romuald Pawluczyk, Conestogo (CA); Duncan MacIntyre, Campbellville (CA); Bronislaw Bednarz, Toronto (CA); Darin L. Farrelly, Fergus (CA); Chris Sterne, London (CA); Ash Kaushal, Mississauga (CA); Mang Li, Waterloo (CA); Kenneth Anthony Morand, Fergus (CA)

(73) Assignee: NIResults Inc. (CA)

( * ) Notice: Subject to any disclaimer, the term of this patent is extended or adjusted under 35 U.S.C. 154(b) by 244 days.

(21) Appl. No.: 10/745,234

(22) Filed: Dec. 22, 2003
(Under 37 CFR 1.47)

Related U.S. Application Data

(60) Provisional application No. 60/435,908, filed on Dec. 20, 2002.

(51) Int. Cl.
*A61B 5/1455* (2006.01)
(52) U.S. Cl. .................................................. 600/322
(58) Field of Classification Search ................. 600/310, 600/316, 335, 322
See application file for complete search history.

(56) References Cited

U.S. PATENT DOCUMENTS

| | | | | |
|---|---|---|---|---|
| 4,975,581 | A * | 12/1990 | Robinson et al. | 600/331 |
| 5,237,178 | A * | 8/1993 | Rosenthal et al. | 250/341.7 |
| 5,361,758 | A | 11/1994 | Hall et al. | |
| 5,372,135 | A * | 12/1994 | Mendelson et al. | 600/322 |
| 5,429,128 | A | 7/1995 | Cadell et al. | |
| 5,452,717 | A * | 9/1995 | Branigan et al. | 600/323 |
| 6,040,578 | A | 3/2000 | Malin et al. | 250/339.12 |
| 6,067,463 | A * | 5/2000 | Jeng et al. | 600/336 |
| 6,113,541 | A * | 9/2000 | Dias et al. | 600/322 |
| 6,167,290 | A | 12/2000 | Yang et al. | 600/322 |
| 6,223,063 | B1 * | 4/2001 | Chaiken et al. | 600/310 |
| 6,236,047 | B1 | 5/2001 | Malin et al. | 250/339.12 |
| 6,292,686 | B1 * | 9/2001 | Chaiken et al. | 600/310 |

(Continued)

FOREIGN PATENT DOCUMENTS

WO      WO 93/16629      9/1993

*Primary Examiner*—Eric F Winakur
(74) *Attorney, Agent, or Firm*—Ballard Spahr (57) ABSTRACT

The present invention provides a method for measuring a blood analyte concentration of a body part comprising removing a portion or all of the blood from the body part to produce a modified body part, and recording a first absorbance value of the modified body part. This is followed by filling the body part with blood to produce a filled body part, and recording a second absorbance value of the filled body part. A difference spectrum is obtained by subtracting the first absorbance values from the second absorbance values, and a calibration algorithm for the blood analyte is applied to the difference spectrum, thereby measuring the concentration of the blood analyte. Also provided is an apparatus for determining the concentration of a blood analyte of a body part. The apparatus comprising a chamber of a size and shape to receive the body part, where the chamber comprises an element for withdrawing and reintroducing blood from the body part, when the body part is inserted within the chamber. The chamber also comprising one or more than one port for introducing electromagnetic radiation into the chamber and onto that body part, and collecting remaining electromagnetic radiation following interaction with the body part.

26 Claims, 8 Drawing Sheets

U.S. PATENT DOCUMENTS 6,372,503 B1 4/2002 Samsoondar .................... 436/8
7,050,842 B2 * 5/2006 Chaiken et al. ............. 600/316
2002/0077535 A1 * 6/2002 Finarov et al. .............. 600/322

* cited by examiner

Heating/cooling elements  31

Temperature sensor  32

Temperature controller

APPARATUS AND METHODS FOR COMPENSATION OF BLOOD VOLUME EFFECTS ON NIR SPECTROSCOPIC MEASUREMENTS OF BLOOD ANALYTES

This application claims benefit of U.S. Provisional Application No. 60/435,908, filed Dec. 20, 2002, which is incorporated herein by this reference.

FIELD OF THE INVENTION

This invention relates to non-invasive measurement of blood analytes by NIR spectroscopy. Particularly, the invention relates to a finger receptor that can minimize errors caused by blood volume effects.

BACKGROUND

There are two major factors that should be considered in Near Infrared (NIR) non-invasive measurement of blood analytes. The first factor is the magnitude of the absorbance of NIR radiation by the analyte, referred to as the analyte signal, and the second factor is the location of analyte in the sample body part that is placed in the path of NIR radiation. Assuming that the analyte signal is adequate for non-invasive measurement of same, the main cause of error may lie in the physiology of the body part placed in the path of electromagnetic radiation. Although reference is made herein to the finger, as is the preferred body part, the finger should not be considered limiting in any way.

In an average young male, 18% of the body weight is protein and related substances, 7% is mineral, and 15% is fat. The remaining 60% is water. The water and its constituents are located in three major compartments: vascular compartment, the interstitial compartment, and the intracellular compartment. The vascular compartment contains blood, which comprises about 40% red blood cells and about 60% plasma. The vascular and interstitial compartments are the major contributors to the extracellular compartment. The intracellular component of the body water accounts for about 55% of the body weight and the extracellular component for about 45%. In terms of volume, the average body water is about 42 L: 23 L intracellular, and 19 L extracellular of which 8 L are interstitial and 3 L plasma. Many factors affect these proportions, e.g., height, weight, gender, diseases, and age. Within an individual, these proportions can also be affected by activity level, diet, hormone fluctuations, pharmaceuticals, and body part.

Although glucose is used for illustration, similar rational can be used for any blood analyte. Ingested glucose that is absorbed into the rich blood supply of the gut, is circulated around the other parts of the body. All the blood in circulation traverses the entire circuit of the circulation system an average of once each minute when the body is at rest, and as many as six times a minute when a person becomes extremely active. The capillaries are the smallest blood vessels with walls of a single layer of cells and of a diameter barely large enough for red blood cells to squeeze through. The capillary walls are permeable to small molecules like water and glucose. As the blood passes through the capillaries the glucose and water rapidly diffuse from the vascular into the interstitial compartments, where the glucose concentration in both vascular and interstitial compartments equilibrate. Most body cells (e.g. muscle cells) require insulin for glucose uptake. The glucose that is internalized into the cell is rapidly metabolized to provide energy, leaving a very low concentration of glucose in the intracellular compartment, causing the compartment of highest fluid volume to have the lowest glucose concentration.

When NIR is transmitted through a human finger, or other body part, all the substances in the light path absorb light according to the number of absorbing elements, including analytes, present, and the absorptivity of each element. As absorbance of the NIR is correlated with a concentration of a substance dissolved in water (i.e., mass per unit volume, e.g., milligrams/deciliter or mg/dL), a calibration algorithm may be used to predict concentration values of one or more than one analyte in the body part. In developing a calibration algorithm, if the appropriate reference values are not used, the algorithm may not predict analyte concentrations accurately. In the case of glucose, plasma glucose concentration may be used as the reference value or independent variable for developing a calibration algorithm. This reference value works well provided that there is good correlation between plasma glucose concentration and glucose concentration of a body part, for example the finger. Development of a calibration algorithm is disclosed in U.S. Pat. No. 6,372,503 (which is incorporated herein by reference).

In the case of hemoglobin, it is normally only located within the red blood cells, which are restricted to the vascular compartment. The vascular compartment contains arterial blood and venous blood, which may be considered to exist in two sub-compartments. The technology of pulse oximetry is well known for its ability to overcome some of these fluid compartment issues. Furthermore, since pulse oximetry is usually used to measure oxygen saturation of hemoglobin (approximately, the ratio of oxy-hemoglobin to the sum of oxy-hemoglobin and deoxy-hemoglobin) in arterial blood, pulse oximetry has overcome the challenge of isolating the absorbance by arterial blood, from the rest of the tissue, including venous blood. However, the art of pulse oximetry cannot be applied to non-invasive measurement of blood analyte concentration.

U.S. Pat. No. 5,361,758 discloses non-invasive measurement of blood analytes using NIR. There is no teaching of the effects of different fluid compartments, and how to overcome these effects, on the accuracy of the measurement of blood analytes.

U.S. Pat. No. 5,429,128 discloses a finger receptor for repeatable non-invasive measurement of blood analytes using NIR. There is no teaching of the complexity of fluid compartments, and how these effects on the accuracy of the measurement of blood analytes may be overcome.

U.S. Pat. No. 6,167,290 discloses the use of a vacuum to increase the amount of blood in the light path in order to enhance the Raman signal. Again, there is no teaching of the complexity of fluid compartments, and how to overcome the effects of the different compartments on the accuracy of the measurement of blood analytes.

Although reference is made to absorbance of electromagnetic radiation, it should be understood that reflectance measurement is also within the scope of this invention. The optical measurement, whether it is absorbance or reflectance, is dependent on analyte concentration in all body compartments measured, as well as the changes in the ratio of tissue fluids, which is altered by activity level, diet or hormone fluctuations, which in turn, affects the glucose measurement.

It is an object of the present invention to overcome disadvantages of the prior art. This object is met by a combination of the features of the main claims. The subclaims disclose further advantageous embodiment of the invention.

SUMMARY OF THE INVENTION

This invention relates to non-invasive measurement of blood analytes by NIR spectroscopy. Particularly, the invention relates to a finger receptor that can minimize errors caused by blood volume effects.

According to the present invention there is provided a method for measuring a blood analyte concentration of a body part comprising:

a) removing a portion or all of the blood from the body part to produce a modified body part;

b) recording first absorbance or reflectance values of the modified body part;

c) filling the body part with blood to produce a filled body part;

d) recording second absorbance or reflectance values of the filled body part;

e) obtaining a difference spectrum by subtracting the first absorbance or reflectance values from the second absorbance or reflectance values;

f) applying a calibration algorithm for the blood analyte to the difference spectrum, thereby measuring the concentration of the blood analyte.

The present invention pertains to the method just described wherein in the step of removing (step (a)), the body part is partially empty of blood.

The present invention also include the method as described above, wherein the blood analyte is selected from the group consisting of: glucose, glycosylated hemoglobin, lactate, pyruvate, total cholesterol, LDL-cholesterol, HDL-cholesterol, triglycerides, total protein, albumin, urea, creatinine, urate, sodium, potassium, chloride, bicarbonate, total hemoglobin, hematocrit, bilirubin, immunoglobulins, transferring and ferritin.

The present invention embraces the method described above wherein in the step of removing (step (a)), blood is removed from a body part, for example a finger by a method selected from the group consisting of: applying positive pressure to any portion of the body part, pulling a tight-fitting sheath away from a tip of the body part, and pulling an O-ring away from the tip of the body part. Additionally, the positive pressure can be delivered by a pneumatic cuff or a piston.

The present invention also provides the method as described above wherein in the step of filling (step (c)), filling is performed by applying a negative pressure to the body part. Preferably the negative pressure is less than that required to rupture one or more blood vessel.

Alternatively, the present invention pertains to the method described above wherein in the step of filling (step (c)), filling is achieved by controlling the temperature of the body part.

The present invention also includes the method described above wherein in the step of applying (step (f)), the calibration algorithm uses one or more wavelengths selected from the range of from about 650 nm to about 2800 nm. Furthermore, the calibration algorithm can be developed using a chemometrics technique selected from the group consisting of: simple linear regression, multiple regression or multivariate analysis.

The present invention provides an apparatus for measuring a blood analyte concentration of a body part comprising:

i) a chamber of a size and shape to receive the body part, the chamber comprising an element for withdrawing and reintroducing blood from the body part, when the body part is inserted within the chamber; and ii) one or more than one port for introducing electromagnetic radiation into the chamber and onto the body part, and collecting remaining electromagnetic radiation following interaction with the body part.

Also included in this invention is the apparatus described above wherein the element for withdrawing and reintroducing blood from the body part comprises an element that applies a positive pressure to one or more than one portion of the body part. Furthermore, the element that applies a positive pressure to one or more than one portion of a body part can be selected from the group consisting of a tight-fitting sheath, an O-ring, a piston, a pneumatic cuff and a bladder.

The present invention relates to the apparatus described above, wherein the chamber further comprises a seal at one end of the chamber, the seal is of a size and shape for receiving the body part, and the seal defining an opening through which the body part may extend when the body part is inserted within the chamber. If the apparatus is fitted with a seal as just described, then the element that applies a positive pressure to one or more than one portion of a body part can be a pressure/vacuum system. Additionally, the element for withdrawing and reintroducing blood from the body part may be an element that controls the temperature of the body part.

The present invention also provides an apparatus as described above, wherein the chamber further comprises one or more than one first optical element for delivering electromagnetic radiation from a radiation source into the chamber through the one or more than one port, and one or more than one second optical element for collecting electromagnetic radiation following interaction with the body part. Furthermore, the apparatus may comprise a spectral analyzer in optical communication with the chamber, the spectral analyzer comprising a calibration algorithm for determining a concentration of the blood analyte.

The present invention pertains to a method for measuring a blood analyte concentration of a body part comprising:

a) filling the body part with blood to produce a filled body part;

b) recording an absorbance or a reflectance value of the filled body part;

c) applying a calibration algorithm for the blood analyte to the absorbance or reflectance value, thereby measuring the concentration of the blood analyte.

This invention also includes the method as just described where the body part is a finger. Furthermore, the present invention provides the method just described, where in the step of filling (step a)), filling is performed by applying a negative or a positive pressure to the body part, and it may be achieved using a pneumatic cuff, a piston, by applying a vacuum, or by controlling the temperature of the body part.

This summary of the invention does not necessarily describe all necessary features of the invention but that the invention may also reside in a sub-combination of the described features.

BRIEF DESCRIPTION OF DRAWINGS

FIG. 2a shows that an O-ring may be applied to the digit, far from the tip, by a cylindrical applicator sized to the finger of the subject. In FIGS. 2b1 and 2b2 the O-ring is rolled toward the tip which forces blood to pool in the fingertip. Rollers can be used to push blood from the base of the finger to the fingertip as shown in FIG. 2c1 and 2c2. FIG. 2d shows the used of an inflatable pressure cuff to push blood from the base of the finger to the fingertip. FIG. 2e shows the use of a mechanical piston can be used to push blood from the base of the finger to the fingertip.

FIG. 5a shows a sheath that fits over the digit that can be used to seal the vacuum/pressure chamber. Sheath sizes can be customized to the individual's finger diameter and length. FIG. 5b shows an annular opening for the digit which allows the digit to enter the vacuum chamber and provides an air seal. The removable annular seal is mounted on the input orifice of the measurement instrument.

FIG. 6a shows the use of a combination of independently controllable chamber vacuum and a pneumatic bladder. The bladder is inflated to mechanically squeeze blood out of the digit. Release of bladder pressure and application of vacuum sucks blood into the fingertip. A feedback controller can be used to stabilize or modulate the pressure and thus regulate the digit blood volume. FIG. 6b shows an embodiment where a combination of vacuum and mechanical pressure is used to modulate the volume of blood in the digit. A mechanical piston physically presses the blood out of the digit. Pressure on the piston is applied by one or more than one spring, an electrical solenoid, or a piezoelectric transducer. A feedback controller can be used to stabilize or modulate the pressure and thus the digit blood volume. One or more vacuum chamber sealing techniques described here can be used for the embodiments shown in FIGS. 6a and 6b.

DESCRIPTION OF THE INVENTION

This invention relates to non-invasive measurement of blood analytes by NIR spectroscopy. Particularly, the invention relates to a finger receptor that can minimize errors caused by blood volume effects.

The following description is of a preferred embodiment by way of example only and without limitation to the combination of features necessary for carrying the invention into effect.

The invention provides, devices and methods for obtaining high accuracy measurements of blood analytes using non-invasive spectroscopic methods. The invention is used to deconvolute analytes (such as glucose) in the physiological vascular (blood) compartment from analytes in non-blood (intracellular and interstitial) compartments of the human or animal body. This can be accomplished, for example, by modulating the blood flow in a region of the animal or human body by mechanical, thermal or other method.

It is to be understood that the concentration of any blood analyte may be determined using the method described herein including but not limited to, glucose, glycosylated hemoglobin, lactate, pyruvate, total cholesterol, LDL-cholesterol, HDL-cholesterol, triglycerides, total protein, albumin, urea, creatinine, urate, sodium, potassium, chloride, bicarbonate, total hemoglobin, hematocrit, bilirubin, immunoglobulins, transferring and ferritin.

The present invention provides a method for measuring a blood analyte concentration of a body part comprising:

a) removing a portion or all of the blood from the body part to produce an modified body part;

b) recording first absorbance values of the modified body part;

c) filling the body part with blood to produce a filled body part;

d) recording second absorbance values of the filled body part;

e) obtaining a difference spectrum by subtracting the first absorbance values from the second absorbance values;

f) applying a calibration algorithm for the blood analyte to the difference spectrum, thereby measuring the concentration of the blood analyte.

The present invention also provides a method for measuring a blood analyte concentration of a body part comprising:

a) filling said body part with blood to produce a filled body part;

b) recording an absorbance or a reflectance value of said filled body part;

c) applying a calibration algorithm for said blood analyte to the absorbance or reflectance value, thereby measuring the concentration of said blood analyte.

Modulating the blood flow in a region of the animal or human body by mechanical, thermal or other method may include filling, emptying and filling, and emptying and partial filling, and uniform or non-uniform ramping of the vascular compartment volume with respect to the other physiological compartments of a desired body part, for example but not limited to a finger. The difference between the baseline (compartments lacking venous or capillary blood), and body signal (all compartments) is predominantly the vascular compartment, which contains the blood analyte of interest. However, emptying of the body part may not always be required in order to obtain an analysis of the analyte of interest within the body part.

While the measurement technique described here is based on near infrared (NIR) absorption spectroscopy, other techniques may also be used, for example and which should not be considered limiting in any way, reflectance, Raman spectroscopy, microwave absorption or other methods which measure noninvasive or with minimum invasiveness, blood analyte concentrations. According to Beer's law, Absorbance=Log (1/Transmitted light), which applies to non-light-scattering samples. The measured parameter is the amount of light transmitted through a sample, and the transmitted light (or transmittance) is then converted to absorbance units. It should be understood that absorbance can be replaced with Log(1/Reflectance), when reflectance is measured instead of transmittance, and reflectance measurement is within the scope of the present invention.

The near infrared region of the electromagnetic spectrum is generally considered to be the spectral interval extending from 650 nm through to 2800 nm and measurements of samples as described herein may be obtained from 650 nm to about 2800 nm, or from about 700 nm to about 1100 nm, or from about 900 nm to about 1600 nm, or from about 1300 nm to about 2500 nm. Absorption bands observed in this interval are primarily the combination and overtone bands of the fundamental infrared bands. Although very weak in intensity, being typically less than one-tenth in intensity of the fundamental infrared bands, these bands are considered to be analytically useful because nearly all chemical species exhibit characteristic absorption bands in this spectral interval. The near infrared region is particularly well-suited to in vivo diagnostic applications because human tissue is essentially transparent to the incident radiation and therefore sufficient penetration of the radiation is possible to allow accurate quantitative analysis.

The source of EMR used in the present invention is preferably near-infrared light, for example but not limited to a polychromatic light source. This type of light source can emit light over a very wide bandwidth including light in the near infrared spectrum. In this case, the light from the light source preferably passes first through a collimator, which is a collection of lenses that concentrate the light into a narrow parallel beam directed at the receptor.

The polychromatic light source can be a quartz-halogen or a tungsten-halogen bulb and is powered by a stabilized power source, for example, a DC power supply, or by a battery. Preferably, the linear array detector has at least ten elements. This polychromatic light source may be a tungsten-halogen lamp or it may be a collection of LEDs or other light sources selected to emit radiation in the desired NIR range.

The apparatus comprises a receptor shaped so that it can be placed in contact with a a body part from a subject. A source electromagnetic radiation (EMR) is feed into the receptor, and following interaction with one or more than one analyte within the body part, the EMR is collected and analyzed. The apparatus may be as described below, or as known in the art, for example, but not limited to those disclosed in U.S. Pat. No. 5,361,758, WO 93/16629, U.S. Pat. No. 6,236,047 or 6,040,578 (all of which are incorporated herein by reference), and modified for use as described herein. The EMR that is collected after interaction with analytes within the body part may be either reflected from, transmitted through, or both reflected from and transmitted through the body part.

The EMR is directed onto, and dispersed by, the body part of the subject. The dispersed light is collected by using any suitable method for example fiber optics, or lenses, and the output signal directed to a diffraction device that separates the wavelengths of light within the output signal into their component parts. Examples of a diffraction device include but are not limited to a diffraction grating or a holographic grating.

The collected signal can comprise EMR that has passed through the body part of the subject or has reflected off the body part, or a combination thereof. The diffracting device preferably disperses the EMR into its component wavelengths so that the infrared region falls along the length of a detector such as, but not limited to a linear array detector (e.g. a 256 element photo diode array), or a CCD. In the case of an array, the detector has a series of diodes and is preferably electronically scanned by a microprocessor to measure the charge accumulated on each diode, the charge being proportional to the intensity of EMR for each wavelength transmitted through or reflected from the tissue in the receptor. The detector is connected to the microprocessor, producing an output spectrum, with the microprocessor analyzing the measurements and ultimately producing a result for each concentration level determined. The result can be stored, shown on a display, or printed on a printer. A keyboard allows a user to control the device, for example, to specify a particular constituent to be measured. The timing and control is activated by the microprocessor to control the device, for example, to determine number and timing of measurements.

Figure 1:
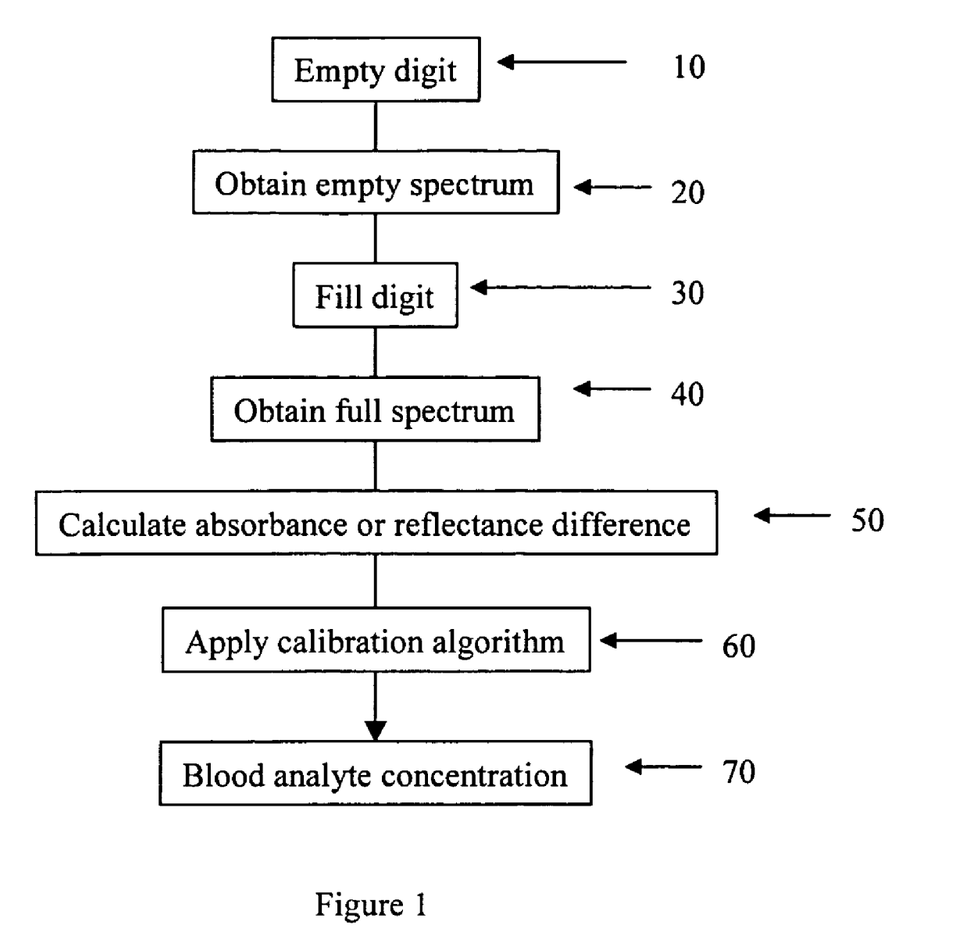
FIG. 1 shows a general procedure for noninvasively measuring concentration of blood analytes via optical absorbance or reflectance methods by a combination of maximizing the blood contribution at the measurement site, and subtracting the absorbance or reflectance, predominantly due to non-vascular tissue. Venous or capillary blood is first evacuated from the area to be tested and a spectrum of the evacuated site is measured (minimum blood absorption/reflectance). The test area is then filled with blood and another spectrum is measured (maximum blood absorbance/reflectance). The blood analyte concentration is then calculated by applying a calibration algorithm to the difference (maximum blood spectrum minus minimum blood spectrum).

With reference to FIG. 1 there is shown an outline of a method of present invention, in this case applied to a human digit or finger. The finger is used here as a non-limiting example of a body part that may be analyzed using the methods described herein. The tissue of the digit is highly perfused, and therefore modulation of the blood flow within the digit may be readily carried out to obtain a blood glucose signal. However, it any other body part is within the scope of this invention, for example but not limited to the ear lobe, web skin between the fingers or toes, skin on the wrist, the palm, the neck, the nose, or any region of skin that is readily drained of blood.

In the example shown in FIG. 1, the digit is emptied (10), by means described below, of blood and an absorbance spectrum is obtained (20). This is referred to as the "empty spectrum" since it represents the digit empty of blood and predominantly contains the interstitial and intracellular compartment signals. However, it is to be understood that the step of emptying may not need to be carried out, and the digit can be filled and a spectrum, either absorbance or reflectance, obtained. If the digit is emptied, the digit is then filled (30) by means described herein, with blood to a maximum level and a second spectrum is obtained (40). This is referred to as the "full spectrum" since it represents the digit full of blood, interstitial fluid and intracellular fluid. The baseline and body signal spectra must each be referenced to an appropriate photometric and wavelength reference for calibration prior to performing the difference function and calculation of the blood analyte concentration (50). The spectrum obtained from the filled digit, or the difference in the absorption or reflectance spectra, in combination with standard chemometric data analysis techniques (60), may be used to calculate, for example, the blood glucose concentration (70). The preferred chemometric data analysis technique is Partial Least squares (PLS), but other types of multivariate analysis techniques, for example Principal Component Regression (PCR) and neural network, are within the scope of the invention, which is obvious to those skilled in the art of chemometrics.

For blood analytes that reside exclusively in the vascular compartment (such as $HbA1_c$), the blood modulation technique described herein advantageously removes extraneous background signals that are not related to compartments and maximizes the signal from the artificially elevated blood volume.

Figure 2:
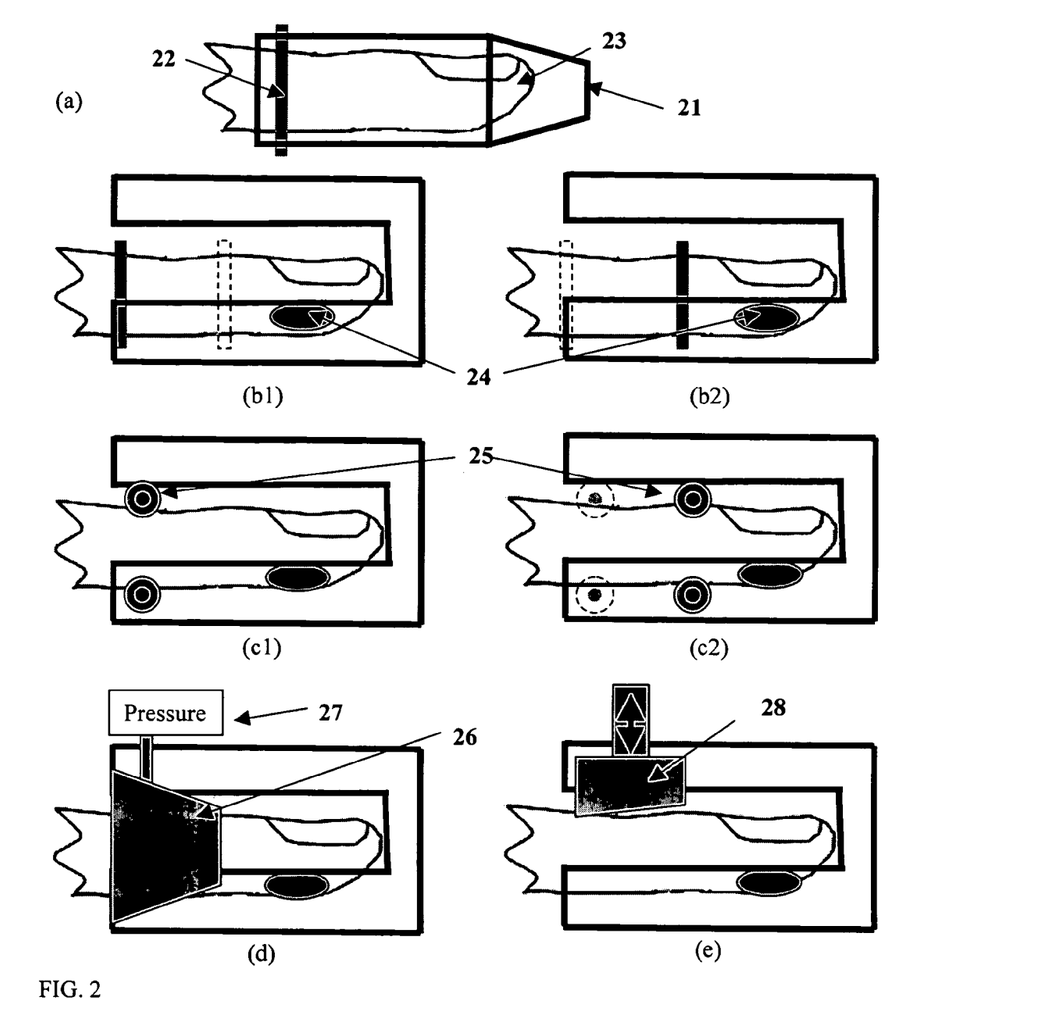
FIG. 2 shows alternate methods for maximizing the blood concentration in a fingertip for noninvasive blood analyte measurements by squeezing blood from the base of the finger to the tip by mechanical means.

Methods of maximizing blood volume in the fingertip include the use of elastic or elastomeric bands, such as O-rings, to constrict the flow of blood into and out of the digit, for example as shown in FIG. 2. It should be understood that O-rings and bands made of any type of suitable material are within the scope of the invention. Shown in FIG. 2a is a tapered cylindrical applicator (21) used to stretch an elastic band (22) to a diameter larger than that of the subject's finger (23). Each patient may have such an applicator sized to his or her individual digit dimensions. The purpose of the applicator is to deposit the band at one or more locations on the digit for the purposes of filling or emptying the digit of blood such as in FIG. 2b1. The band is deposited at the tip of the digit (e.g. dashed outline) and rolled toward the small metacarpal joint forcing the blood away from the tip, thus emptying it. The fingertip is filled as shown in FIG. 2b2 where the band is deposited far from the tip (dashed outline) and rolled toward the nail thus filling the tip with blood. Alternatively, a tight-fitting sheath may be used to withdraw blood from the body part. The sheath may be made of an elastomeric material. Illumination and detection of light is through the optical ports 24, for example as described in U.S. Pat. No. 5,429,128 (which is incorporated herein by reference). As the fingertip blood is cut off from a fresh supply of oxygen, this approach for blood volume modulation may require compensation for oxygenation level of the blood.

Figure 7:
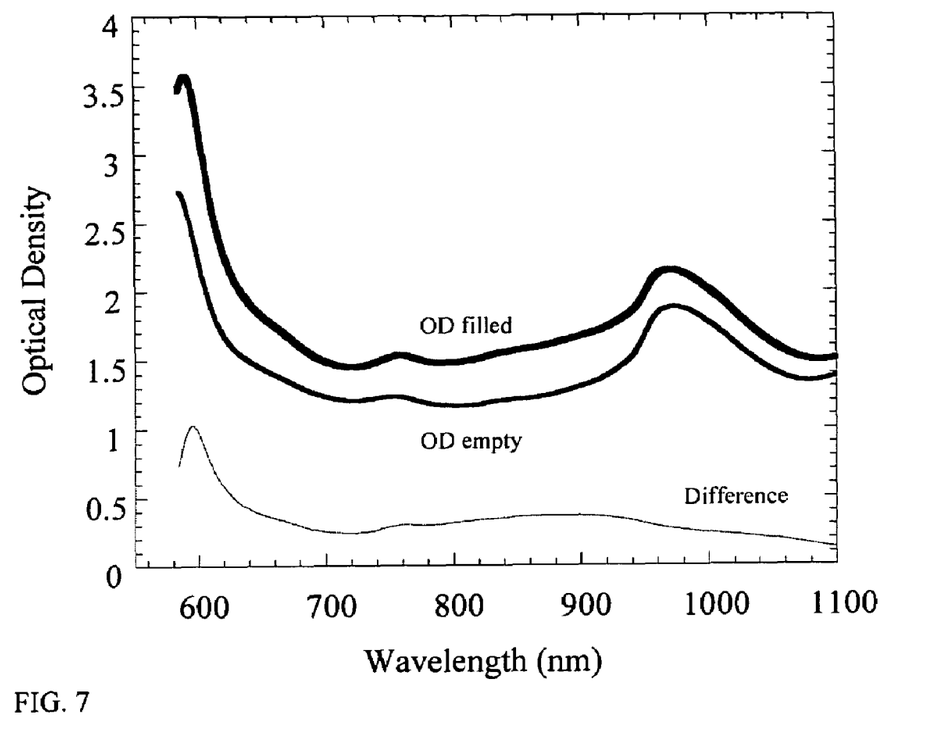
FIG. 7 shows a graphical representation of the absorbance resulting from modulation of finger blood flow with finger constriction using an elastic O-ring. The top curve, which has the highest absorption, is the absorbance spectrum of a blood filled finger (OD filled). The middle curve is the absorbance spectrum for the finger emptied of blood (OD empty), and the lower curve is the difference in the absorption of the filled and empty finger (difference).

FIG. 7 shows an absorption spectrum of a digit that has been manipulated using O-ring modulation of fingertip blood volume as described above. Optical absorption versus pixel number (which corresponds to wavelength) is plotted for a subject with finger filled (OD filled; top curve) and finger empty (OD empty; middle curve). The bottom curve is the difference between the two absorption spectra (Difference) as described in the method for FIG. 1. A maximum optical density difference of approximately 1 OD is observed in the hemoglobin wavelength range.

One, or more than one roller (25) such as depicted in FIG. 2c1 may also be used to, fill, or empty and fill, the area to be measured with blood. This approach uses a similar modulation technique to that of the elastic band but differs in that the measurement instrument contains rollers that may be operated automatically by the instrument under computer control. This enables real time monitoring and control of the blood volume in the tip of the digit by optical techniques, and may be used to provide actuation of the rollers when a filled, empty, or an intermediate state is reached. The one or more than one roller also enables time dependent variation of the blood volume, for example, linear, quadratic, sinusoidal, etc., to be obtained, which can be useful in elucidating and correcting for inter-subject and intra-subject physiological variations.

With reference to FIG. 2d, blood can also be squeezed toward the extremities of a digit by use of an inflatable pneumatic cuff (26). The cuff may be part of the instrument, or alternatively can be worn by the subject. The cuff is designed to constrict the digit first at the base and progressively constrict toward the tip. The pressure in the cuff and the inflation level can be governed by a feedback pressure control system (27). A computer can control the cuff pressure, and thus the tip blood volume, either in open (preset pressures) or closed loop (real time) feedback control. The latter could be useful in elucidating and correcting for inter-subject and intra-subject physiological variations.

A mechanical piston (28; FIG. 2e) can also be used to constrict the digit at the base and progressively constrict the digit toward the tip as piston pressure is applied. Preferably the piston is wedge-shaped as shown, but other shapes, for example a curved bottom, which should not be considered limiting in any way, may be used. The piston tip can be made of soft, semi-flexible material such as to conform to the finger topology and patient comfort. A computer can control the piston pressure, and thus the tip blood volume, either in open (preset pressures) or closed loop (real time) feedback control. The latter could be useful in elucidating and correcting for inter-subject and intra-subject physiological variations. It should be understood that pistons made from any type of material are within the scope of the invention.

The apparatus shown in FIG. 2e can also be used to apply pressure to the tip for a period of time. Natural vascular dilation after constriction occurs, as the circulatory system attempts to compensate for the previously reduced tissue oxygen level. When the pressure is released, the blood flows back into the tip through dilated blood vessels at a higher volume than before providing a higher signal.

Figure 3:
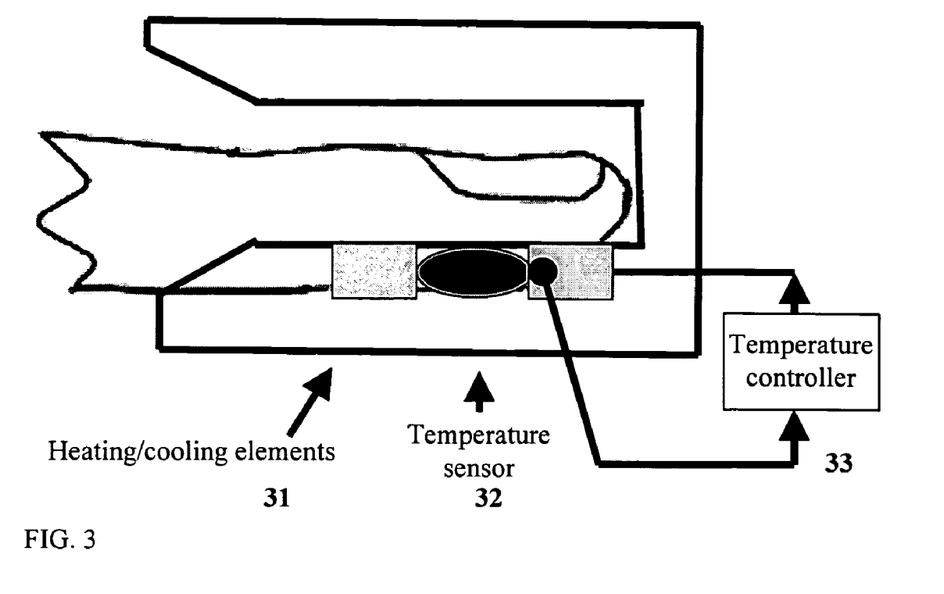
FIG. 3 shows a method for controlling the blood concentration in a fingertip by controlling the temperature of the digit in a chamber. A temperature control system consisting of heating/cooling elements, and temperature sensing elements are shown.

Change in vascular dilation associated with temperature can also be used to modulate the blood flow and thus volume in the tip. This may be used if reduced instrumentation complexity is desired as there are no moving parts. Heating and cooling elements (31) are placed surrounding the optical port in intimate contact with the finger. The finger receptor is thermally insulated from the heating and cooling element such that the primary temperature change is in the finger. A temperature sensor (32) is placed in intimate contact with the finger to monitor surface temperature of the digit. A temperature controller (33) provides the closed loop feedback control of the digit temperature and can modulate the tip blood volume in a linear, nonlinear, or sinusoidal fashion. The latter could be useful in elucidating and correcting for inter-subject and intra-subject physiological variations.

Figure 4:
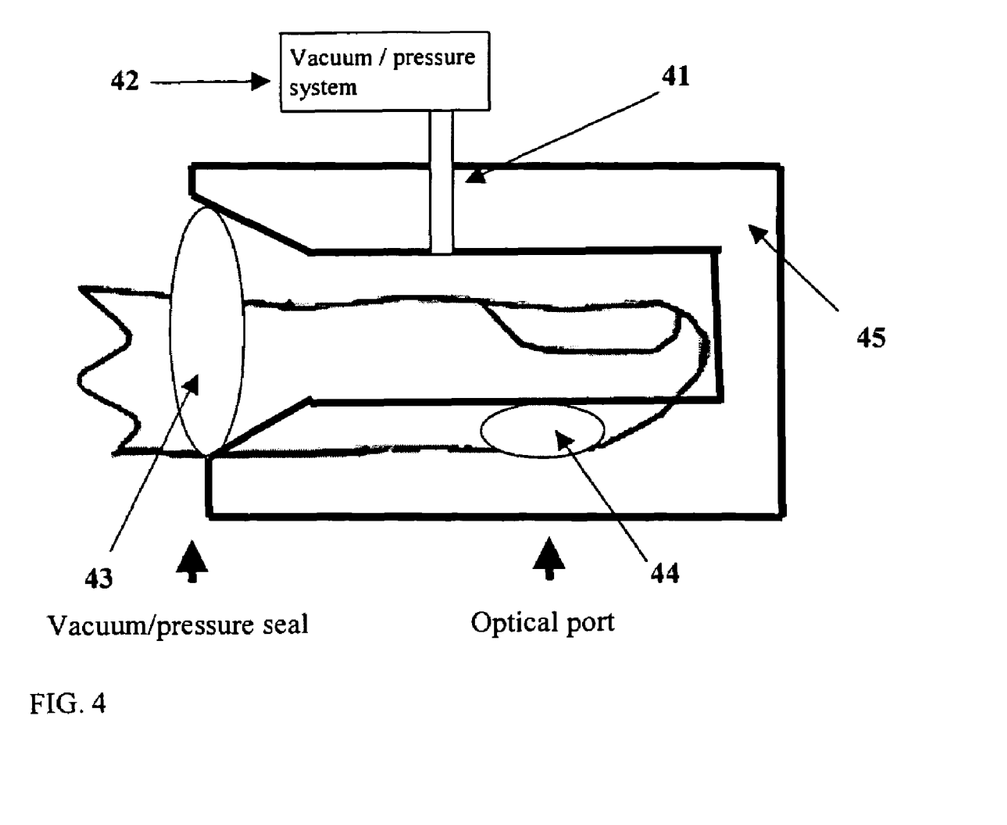
FIG. 4 shows a method for controlling the blood concentration in a fingertip by application of vacuum to the digit in a chamber. The finger chamber contains one or more vacuum ports connected to a vacuum system that controls the positive and negative pressure around the digit to control or modulate the volume of blood in the digit. The chamber is sealed by one or more than one pressure seal.

In an alternate example, pneumatic pressure or vacuum can be used to modulate blood volume in a body part, for example the digit. A finger receptor can be constructed such as shown in FIG. 4 which consists of a chamber (45) having a vacuum port (41) which is connected to a vacuum/pressure system (42) that is manually or computer controllable. This chamber can be either larger or smaller than the human or animal body part being tested. Optical ports (44) are sealed, for example by epoxies, glues, o-rings, flanges or other standard pressure sealing techniques. An air or gas vacuum/pressure seal (43) closes the chamber opening to maintain a controlled internal pressure. Application of a positive pressure into the chamber uniformly squeezes the digit thus forcing blood out of the digit to provide the "empty" blood volume. A vacuum, or negative pressure, may also be applied to the chamber to draw blood into the digit to achieve and maintain an equilibrium or static blood flow in the digit. This will provide a "filled" blood volume. Intermediate blood volumes can be achieved by adjusting the pressure of the finger receptacle. A computer can control the chamber pressure, and thus the tip blood volume, either in open (preset pressures) or closed loop (real time) feedback control. The latter could be useful in elucidating and correcting for inter-subject and intra-subject physiological variations. The applied vacuum or pressure should not be so high as to break capillaries and distribute blood into the interstitial and intracellular compartments.

Application of positive and negative pressure to empty and fill the finger respectively can be combined with a method of restricting blood by elastic bands or other methods, as desired. For example, which is not to be considered limiting in any manner, the digit can be inserted into a tubular applicator (21), such as described in FIG. 2a, whose pressure is controlled by a pressure/vacuum system connected to the tubular applicator (21). The elastic band (22) can be applied onto the digit when the digit reaches the desired fill state in order to maintain it in that state. The digit is then removed from the vacuum system and subsequently inserted into the instrument for the optical measurement of blood analytes.

Figure 5:
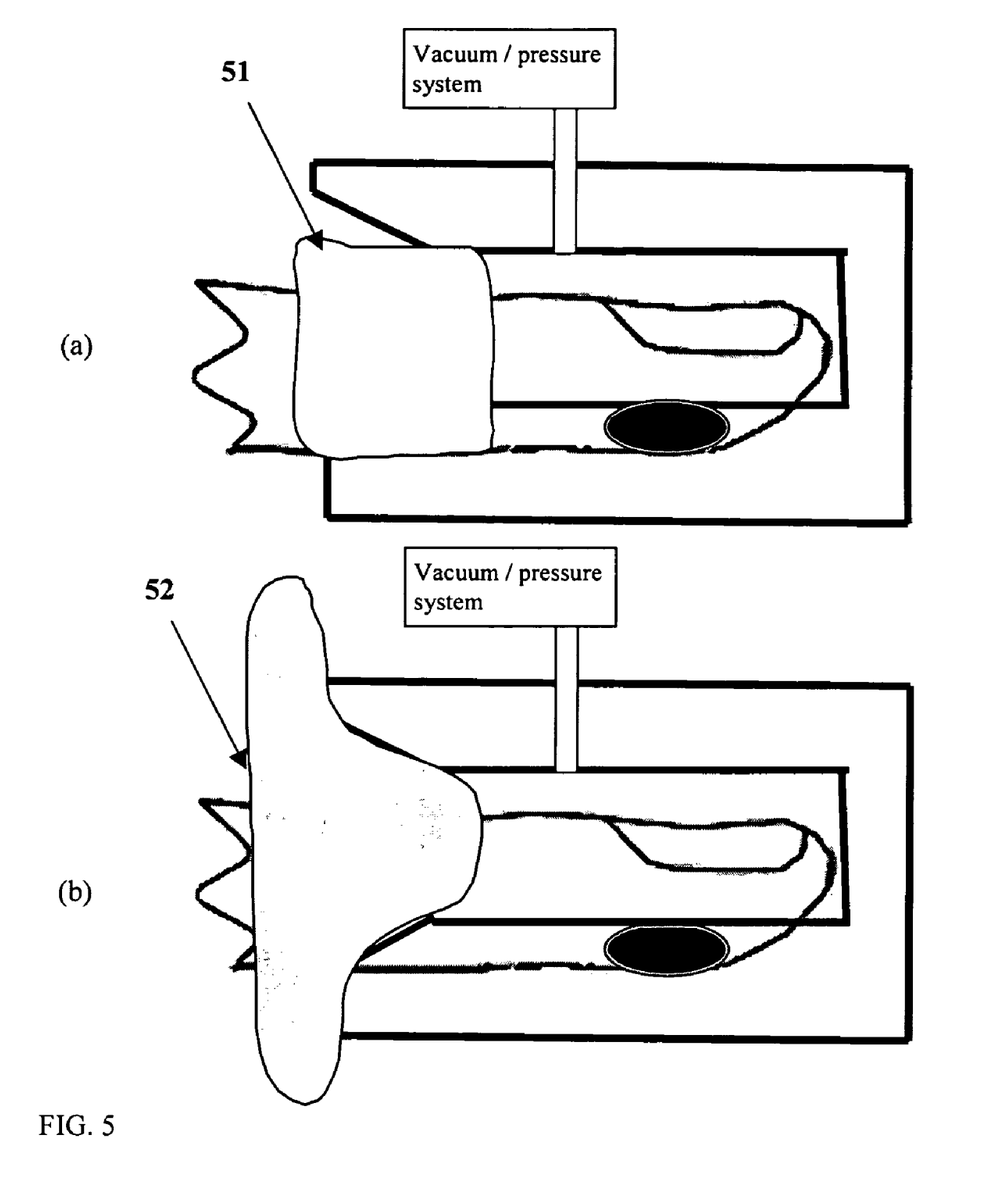
FIG. 5 shows two embodiments of pressure seals for the digit chamber.

Examples of several non-limiting pressure seals that can be used are shown in FIG. 5. With reference to FIG. 5a there is shown a sleeve (51) that fits around the digit. The sleeve can be constructed of rubber, sponge rubber, urethanes, plastics, leather, cork or other suitable materials. The finger and sleeve (51) are inserted into the chamber (45) such that an air seal is made. Pressure is controlled as previously described, using a vacuum/pressure system (42) in order to modulate the blood volume in the finger for blood analyte measurement.

Alternatively, an annular vacuum/pressure seal (52; FIG. 5) can be mounted onto the instrument, for example the chamber (45), through which a digit is inserted. This seal can be constructed of rubber, sponge rubber, urethanes, plastics, leather, cork or other suitable materials. This seal can also be replaceable to accommodate different finger sizes. Pressure is controlled as previously described, using a vacuum/pressure system (42), in order to modulate the blood volume in the finger for blood analyte measurement.

Figure 6:
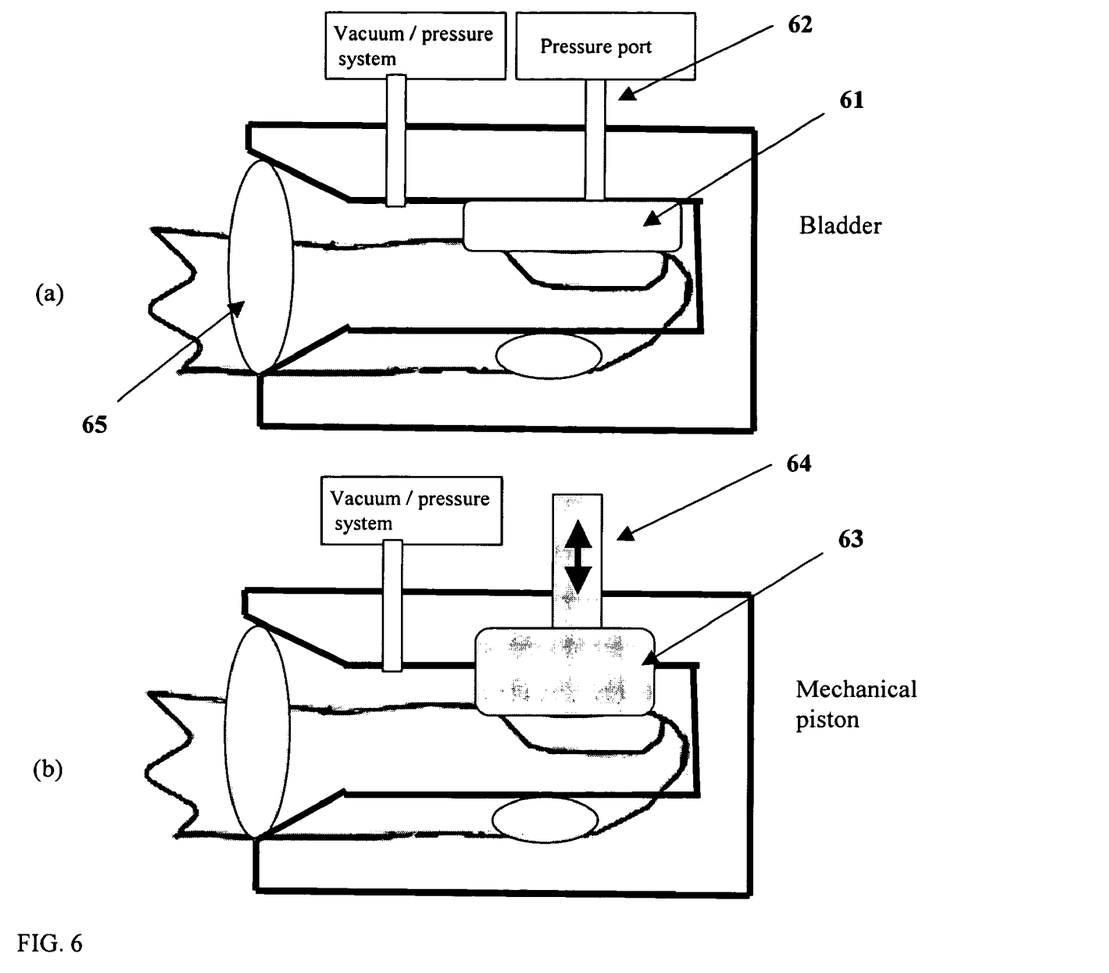
FIG. 6 shows two methods of using differential pressure to modulate the blood volume in a digit.

It may be desirable to combine pneumatic pressure/vacuum with mechanical pressure to modulate blood volume in the region to be measured by optical means as shown in FIG. 6. FIG. 6a shows a digit vacuum chamber (45) having a seal (65), a vacuum/pressure system (42) as previously described and an additional pressure port (62) on which an inflatable bladder (61) is placed. The bladder (61) is constructed from rubber, sponge rubber, urethanes, plastics, leather, cork or other pliable materials that can be formed to hold pressure. The bladder (61) is pneumatically independent from the vacuum/pressure system (42) of the chamber (45), and is used to apply mechanical pressure directly to the fingertip. Thus the fingertip pressure is controlled independently from that of the remaining finger by two separate pneumatic systems. This may be desired since just the fingertip can be emptied of blood as opposed to the entire finger allowing for a faster modulation of fingertip blood volume. A computer can control the chamber (42) and bladder pressures (61, 62), and thus the tip blood volume, either in open (preset pressures) or closed loop (real time) feedback control. The latter could be useful in elucidating and correcting for inter-subject and intra-subject physiological variations. The applied vacuum or pressure should not be so high as to break capillaries and distribute blood into the interstitial and intracellular compartments.

It may also be advantageous to use a mechanical piston (63; FIG. 6b) to apply pressure directly to the fingertip. The piston tip can be made of soft, semi-flexible material such as to conform to the finger topology and patient comfort. Alternatively, pneumatic pressure could be applied via a pressure port (64), which pushes the piston (63) against the finger, thus emptying the fingertip. A computer can control the piston pressure, and thus the tip blood volume, either in open (preset pressures) or closed loop (real time) feedback control. The latter could be useful in elucidating and correcting for inter-subject and intra-subject physiological variations.

Therefore, the present invention also provides an apparatus for measuring a blood analyte concentration of a body part comprising:

i) a chamber of a size and shape to receive the body part, the chamber comprising an element for withdrawing and reintroducing blood from the body part, when the body part is inserted within the chamber; and ii) one or more than one port for introducing electromagnetic radiation into the chamber and onto the body part, and for collecting electromagnetic radiation following interaction with the body part.

Non-limiting examples of the element for introducing, or withdrawing and reintroducing blood from the body part include an element that applies a positive pressure to one or more than one portion of the body part, for example a tight-fitting sheath, an O-ring, a piston, a pneumatic cuff, a pressurizable bladder, or an element that controls the temperature of the body part. Furthermore, the chamber may further comprise a seal at one end of the chamber, where the seal is of a size and shape for receiving the body part, and comprises an opening through which the body part may pass when the body part is inserted within the chamber. If the chamber is fitted with a seal, then the element that applies a positive pressure to one or more than one portion of a body part may further comprise a pressure/vacuum system.

Figure 8:
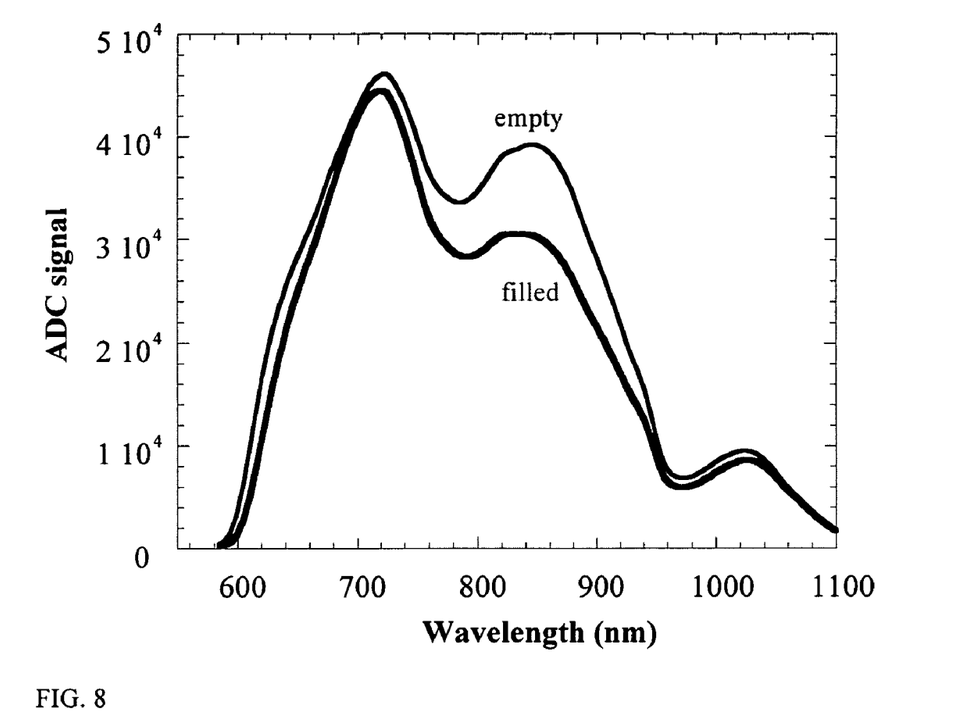
FIG. 8 shows a graphical representation of the digital sensor response resulting from modulation of finger blood flow with mechanical pressure applied by a spring-loaded piston. The upper curve (empty) is the absorbance spectrum of fingers under pressure. The loser curve (filled) is the absorbance spectrum of fingers without finger pressure. Four subjects were tested each having eight measurements.

The chamber may further be in optical communication with a spectrum analyzer as are known in the art. In this regard, the chamber may be fitted with one or more than one optical element for delivering electromagnetic radiation from a radiation source into the chamber through the one or more than one port, and for collecting electromagnetic radiation following interaction with the body part. The spectrum analyzer may then be used to determine the spectral composition of received radiation, from both an "empty" body part and a "filled" body part as described herein, and from a difference spectrum (e.g. FIGS. 7 and 8), determine the analyte concentration for example using a method as disclosed in U.S. Pat. No. 6,372,503 (which is incorporated herein by reference).

The process of determination of analyte concentration in a body part may be accomplished by using an order derivative of the absorbance, including zero order, optionally combined with other forms of data pre-processing. Photometric correction may or may not be necessary, depending on the required accuracy of the predicted analyte concentration. Any statistical technique may be used to derive the primary calibration algorithm, for example, which should not be considered limiting in any way, simple linear regression, multiple linear regression, and multivariate data analysis. Examples of multivariate data analysis, which should not be considered limiting in any way, are Principal Component Analysis (PCA), Principal Component Regression (PCR), Partial Least Squares regression (PLS), and Neural networks. Examples of data pre-processing which should not be considered limiting in any way, include smoothing, deriving a first and higher order derivative of absorbance, interpolation of absorbance, multiplicative scatter correction, photometric correction, and data transformation, for example Fourier transformation. Preferably, the calibration algorithm is applied to the absorbance data of future samples after data pre-processing. In a preferred embodiment, the form or combination of forms of data pre-processing used should be the same as used prior to primary calibration algorithm development.

As an example, where an order derivative of absorbance is used, photometric correction may or may not be necessary, provided that the order of derivative of absorbance used in the primary calibration algorithm at the selected wavelength(s) does not contain significant inter-apparatus variability, although the interpolated absorbances of the same sample for at least one of a standard set of wavelengths may contain significant variability. It is well known that absorbance variability can be removed in certain sections of the absorbance spectra, by using an order of derivative of the absorbance. The acceptable variability in the derivative of the absorbance(s) at the wavelength(s) chosen for the calibration depends upon the inter-apparatus variability in the predicted value of the analyte. Smoothing, data transformation, and obtaining higher than zero order absorbance are non-limiting examples of data pre-processing. Another method of data pre-processing is Multiplicative Scatter Correction, which can minimize absorbance variability. Data pre-processing can be included in the statistical technique used to develop primary calibration algorithms. Data preprocessing may also facilitate calibration algorithm transfer with or without the use of photometric correction. Multiplicative scatter correction may also be used, when spectrophotometric data from more that one apparatus is combined.

According to the approach of using an order derivative of absorbance, while the first derivative of absorbance removes most variability between a first and second apparatus, higher derivatives, while still useful and within the scope of the present invention, tend to introduce sharper peaks and accordingly are not as preferred as the first derivatives. Derivatives of absorbance beyond the $2^{nd}$ increase the complexity of the spectra and magnify the noise i.e., the signal to noise ratio decreases. Because the peaks are sharper with the higher order of derivatives, wavelength accuracy becomes more critical for accurate determination of analyte concentration. Multivariate data analysis can be also be used to remove most variability between a first and second apparatus, and therefore the use of zero order derivative of absorbance is within the scope of this invention. The actual order derivative of absorbance and the statistical technique used, with the options of photometric correction and other forms of data pre-processing, depends on the required accuracy of the predicted value of the analyte.

The above description is not intended to limit the claimed invention in any manner, furthermore, the discussed combination of features might not be absolutely necessary for the inventive solution.

All citations are herein incorporated by reference.

The present invention has been described with regard to preferred embodiments. However, it will be obvious to persons skilled in the art that a number of variations and modifications can be made without departing from the scope of the invention as described herein.

We claim:

1. A method for measuring a blood analyte concentration of a body part comprising:
    a) removing a portion or all of the blood from said body part by rolling an elastic band along said body part, or by applying a positive pressure to said body part using a pressure/vacuum system, to produce a modified body part;
    b) recording first absorbance values of said modified body part;
    c) filling said modified body part with blood to produce a filled body part;
    d) recording second absorbance values of said filled body part;
    e) obtaining a difference spectrum by subtracting said first absorbance values from said second absorbance values; and
    f) applying a calibration algorithm for said blood analyte to the difference spectrum to measure the concentration of said blood analyte.

2. The method of claim 1 wherein in said step of removing (step (a)), said modified body part is partially empty of blood.

3. The method of claim 1 wherein said body part is a finger.

4. The method of claim 1 wherein said blood analyte is selected from the group consisting of: glucose, glycosylated hemoglobin, lactate, pyruvate, total cholesterol, LDL-cholesterol, HDL-cholesterol, triglycerides, total protein, albumin, urea, creatinine, urate, sodium, potassium, chloride, bicarbonate, total hemoglobin, hematocrit, bilirubin, immunoglobulins, transferrin and ferritin.

5. The method of claim 1 wherein in said step of filling (step (c)), filling is performed by applying a negative pressure to said body part.

6. The method of claim 5 wherein said negative pressure is less than that required to rupture one or more than one blood vessel.

7. The method of claim 1 wherein in said step of filling (step (c)), filling is achieved by controlling the temperature of said body part.

8. The method of claim 1 wherein in said step of applying (step (f)), said calibration algorithm uses one or more wavelengths selected from the range of from about 650 nm to about 2800 nm.

9. The method of claim 1 wherein in said step of applying (step (f)), said calibration algorithm is developed using a chemometrics technique selected from the group consisting of: simple linear regression, multiple regression or multivariate analysis.

10. The method of claim 1, wherein in said step of removing (step (a)), a portion or all of the blood from said body part is removed by rolling an elastic band along said body part.

11. An apparatus for measuring a blood analyte concentration of a body part, comprising:
    i) a chamber of a size and shape to receive said body part, said chamber comprising an elastic band for withdrawing and reintroducing blood from said body part when said body part is inserted within the chamber,
    ii) one, or more than one, port for introducing electromagnetic radiation into the chamber and onto said body part, and collecting remaining electromagnetic radiation following interaction with said body part, and
    iii) a processor configured to determine a blood analyte concentration from a difference spectrum obtained by subtracting measurements obtained after at least a portion of the blood from said body part has been withdrawn, from measurements obtained after the blood has been reintroduced into said body part.

12. The apparatus of claim 11, wherein the chamber further comprises a seal at one end of the chamber, said seal of a size and shape for receiving said body part, and said seal defining an opening through which said body part may pass when said body part is inserted within said chamber.

13. The apparatus of claim 11 wherein said chamber is sized and shaped to fit a finger.

14. The apparatus of claim 11, wherein said chamber further comprises one or more than one first optical element for delivering electromagnetic radiation from a radiation source into said chamber through the one or more than one port, and one or more than one second optical element for collecting electromagnetic radiation following interaction with said body part.

15. A method for measuring a blood analyte concentration of a body part comprising:
    a) removing a portion or all of the blood from said body part by rolling an elastic band along said body part, or by applying a positive pressure to said body part using a pressure/vacuum system, to produce a modified body part;
    b) recording first reflectance values of said modified body part;
    c) filling said modified body part with blood to produce a filled body part;

d) recording second reflectance values of said filled body part;

e) obtaining a difference spectrum by subtracting said first reflectance values from said second reflectance values, and f) applying a calibration algorithm for said blood analyte to the difference spectrum to measure the concentration of said blood analyte.

16. The method of claim 15, wherein in said step of removing (step (a)), said modified body part is partially empty of blood.

17. The method of claim 15, wherein said body part is a finger.

18. The method of claim 15, wherein said blood analyte is selected from the group consisting of: glucose, glycosylated hemoglobin, lactate, pyruvate, total cholesterol, LDL-cholesterol, HDL-cholesterol, triglycerides, total protein, albumin, urea, creatinine, urate, sodium, potassium, chloride, bicarbonate, total hemoglobin, hematocrit, bilirubin, immunoglobulins, transferrin and ferritin.

19. The method of claim 15, wherein in said step of filling (step (c)), filling is performed by applying a negative pressure to the finger.

20. The method of claim 19, wherein said negative pressure is less than that required to rupture one or more than one blood vessel.

21. The method of claim 15, wherein in said step of filling (step (c)), filling is achieved by mechanical or pneumatic pressure.

22. The method of claim 21, wherein fullness of blood in said finger is maintained by application of a tight-fitting sheath or O-ring.

23. The method of claim 15, wherein in said step of filling (step (c)), filling is achieved by temperature control of said body part.

24. The method of claim 15, wherein in said step of applying (step (f), said calibration algorithm uses one or more wavelengths selected from the range of from about 650 nm to about 2800 nm.

25. The method of claim 15, wherein in said step of applying (step (f)), said calibration algorithm is developed using a chemometrics technique selected from the group consisting of: simple linear regression, multiple regression or multivariate analysis.

26. The method of claim 15, wherein in said step of removing (step (a)), a portion or all of the blood from said body part is removed by rolling an elastic band along said body part.

\* \* \* \* \*